(12) United States Patent
Calvert

(10) Patent No.: US 10,561,355 B2
(45) Date of Patent: Feb. 18, 2020

(54) METHOD OF MANUFACTURING A SKIN PRICKING LANCET

(71) Applicant: OWEN MUMFORD LIMITED, Oxfordshire (GB)

(72) Inventor: Jack Calvert, Oxfordshire (GB)

(73) Assignee: OWEN MUMFORD LIMITED, Woodstock (GB)

( * ) Notice: Subject to any disclaimer, the term of this patent is extended or adjusted under 35 U.S.C. 154(b) by 618 days.

(21) Appl. No.: 15/103,127

(22) PCT Filed: Dec. 9, 2014

(86) PCT No.: PCT/GB2014/053642
§ 371 (c)(1),
(2) Date: Jun. 9, 2016

(87) PCT Pub. No.: WO2015/087064
PCT Pub. Date: Jun. 18, 2015

(65) Prior Publication Data
US 2016/0317072 A1    Nov. 3, 2016

(30) Foreign Application Priority Data

Dec. 10, 2013 (GB) .................... 1321828.4

(51) Int. Cl.
*A61B 5/15* (2006.01)
*A61B 5/151* (2006.01)
(52) U.S. Cl.
CPC ...... *A61B 5/150297* (2013.01); *A61B 5/1411* (2013.01); *A61B 5/150022* (2013.01);
(Continued)

(58) Field of Classification Search
CPC ............ A61B 5/150297; A61B 5/1411; A61B 5/150022; A61B 5/150412;
(Continued)

(56) References Cited

U.S. PATENT DOCUMENTS 5,026,388 A    6/1991  Ingalz
5,304,192 A *  4/1994  Crouse ............... A61B 5/15142
                                            606/167
(Continued)

FOREIGN PATENT DOCUMENTS

CN    101018505 A    8/2007
CN    201303942 Y    9/2009
(Continued)

OTHER PUBLICATIONS

Chinese Office Action dated Oct. 16, 2018 in corresponding Chinese Patent Application No. 201480067250.5.
(Continued)

*Primary Examiner* — Vy Q Bui
(74) *Attorney, Agent, or Firm* — Young & Thompson

(57) ABSTRACT

A method of manufacturing a skin pricking lancet includes: thermoforming a plastic component; locating the thermoformed component and, optionally, one or more further plastic components around a lancet mechanism; and joining the located component(s) to form a hermetically sealed enclosure surrounding the lancet mechanism, the component(s) being formed and joined to provide a housing that structurally supports the lancet mechanism during use, and a cap breakable from the housing to facilitate firing of the lancet mechanism.

8 Claims, 12 Drawing Sheets

(52) U.S. Cl.
CPC ....... *A61B 5/15111* (2013.01); *A61B 5/15117* (2013.01); *A61B 5/15144* (2013.01); *A61B 5/150412* (2013.01); *A61B 5/150549* (2013.01); *A61B 5/150648* (2013.01); *A61B 5/150786* (2013.01)

(58) Field of Classification Search
CPC ........ A61B 5/150549; A61B 5/150648; A61B 5/150786; A61B 5/15111; A61B 5/15117; A61B 5/15144
USPC .................................................. 606/181–185
See application file for complete search history.

(56) References Cited

U.S. PATENT DOCUMENTS

| | | | |
|---|---|---|---|
| 5,389,177 | A | 2/1995 | Shuert |
| 5,554,166 | A * | 9/1996 | Lange .............. A61B 5/150022 600/583 |
| 6,102,927 | A | 8/2000 | Wright |
| 6,168,606 | B1 | 1/2001 | Levin et al. |
| 6,299,626 | B1 | 10/2001 | Viranyi |
| 7,727,166 | B2 | 6/2010 | Fowler et al. |
| 8,066,728 | B2 | 11/2011 | Schraga |
| 8,333,781 | B2 * | 12/2012 | Karbowniczek ..... A61B 5/1411 606/182 |
| 8,449,480 | B2 | 5/2013 | Fowler et al. |
| 8,469,986 | B2 | 6/2013 | Schraga |
| 9,055,899 | B2 | 6/2015 | Lamps et al. |
| 9,131,954 | B2 | 9/2015 | Hong |
| 2006/0116705 | A1 | 6/2006 | Schraga |
| 2006/0253146 | A1 | 11/2006 | Marshall et al. |
| 2009/0043325 | A1* | 2/2009 | Fritz ................ A61B 5/150022 606/181 |
| 2011/0029006 | A1 | 2/2011 | Leong |
| 2011/0098735 | A1 | 4/2011 | Lamps et al. |
| 2012/0123459 | A1 | 5/2012 | Ruf |
| 2013/0066353 | A1 | 3/2013 | Hong |
| 2014/0052023 | A1 | 2/2014 | Starnes |
| 2015/0316485 | A1* | 11/2015 | List ........................ G01N 21/78 435/287.9 |

FOREIGN PATENT DOCUMENTS

| | | |
|---|---|---|
| CN | 201333040 Y | 10/2009 |
| CN | 201642036 | 11/2010 |
| CN | 103179903 A | 6/2013 |
| GB | 2 440 118 A | 1/2008 |
| JP | H05-088503 | 12/1993 |
| JP | 2005-185378 | 7/2005 |
| JP | 2011-530317 | 12/2011 |
| JP | 2013-515510 | 5/2013 |
| JP | 2013-542044 | 11/2013 |
| TW | 200901938 A | 1/2009 |
| WO | 02/43591 A2 | 6/2002 |
| WO | 02/065910 A1 | 8/2002 |
| WO | 2007/086843 A2 | 8/2007 |
| WO | 2011/050142 A1 | 4/2011 |
| WO | 2013-110953 | 8/2013 |

OTHER PUBLICATIONS

Japanese Office Action for Application No. 2016-538502, dated Sep. 25, 2018, with English translation provided.
International Search Report, dated May 12, 2015, from corresponding PCT Application.
GB Search Report, dated Jul. 4, 2014, from corresponding GB Application.
GB Further Search Report, dated Nov. 21, 2014, from corresponding GB Application.

* cited by examiner

METHOD OF MANUFACTURING A SKIN PRICKING LANCET

TECHNICAL FIELD

The present invention relates to skin pricking lancets.

BACKGROUND

In the medical and related diagnostic and testing fields, it is often required to take small samples of blood from a subject for the purpose of testing or analysing the blood. A common way of achieving this is by using a small needle or blade to pierce the skin at a location where blood vessels are close to the surface. The combination of a needle or blade and its carrier is commonly known as a "lancet".

Lancets are typically one-time use devices, with further use of a contaminated lancet giving rise to a risk of infection. Due to this single use nature, it is desirable that lancets are of low cost to manufacture, whilst at the same time being extremely reliable and easy to use. One such device is described in EP0293092. A significant element of the manufacturing cost of lancets is the need to ensure sterilisation. This is often achieved by a post-manufacture irradiation process, where sealed devices are exposed to a dose of radiation. The dose increases with the mass of the lancet, as does the cost.

Many available lancets are provided with removable caps which help maintain sterility, and protect a user from accidental injury. The cap is removed to expose the lancet and may inadvertently be replaced after use. However, once the cap is replaced, it may not be obvious to a user that the lancet has been used. While it may not be possible to reuse the lancet, removing a cap of a used lancet would be unhygienic and potentially frustrating for the user. An additional risk is that a cap is removed and inadvertently replaced without the device having been used, which could result in the lancet being used after its sterility has been compromised by exposure to the atmosphere.

SUMMARY

It is an object of the present invention to provide a skin pricking lancet which is relatively low cost to manufacture.

According to a first aspect of the present invention there is provided a method of manufacturing a skin pricking lancet. The method comprises; thermoforming a plastic component; locating the thermoformed component and, optionally, one or more further plastic components around a lancet mechanism; and joining the located component(s) to form a hermetically sealed enclosure surrounding the lancet mechanism, the component(s) being formed and joined to provide a housing that structurally supports the lancet mechanism during use, and a cap breakable from the housing to facilitate firing of the lancet mechanism.

As an option the method further comprises thermoforming said one or more further components. Optionally, the method further comprises joining the located component(s) together by heat sealing abutting peripheral edges of the component(s). The enclosure may be irradiated in order to sterilise the interior of the enclosure including the lancet mechanism. Optionally, the or each thermoformed component forms both a part of the cap and a part of the housing. A narrowing may be formed at the junction between the housing and the cap of the enclosure.

According to a second aspect of the present invention there is provided a skin pricking lancet comprising an enclosure containing a lancet mechanism, the enclosure comprising one or more plastic components hermetically sealed together, the or at least one plastic component being formed by thermoforming, the enclosure defining a housing and cap such that permanent removal of the cap from the housing can be achieved by breaking the cap from the housing.

As an option the skin pricking lancet comprises a plurality of plastic components all of which are formed by thermoforming.

The plurality of plastic components may comprise two thermoformed plastic components of substantially identical configuration, and the seal between the components may lie substantially in a plane that is parallel to a firing axis of the lancet mechanism. As an option the enclosure comprises a relatively narrow neck region between the housing and the cap to facilitate breaking of the cap from the housing.

According to a third aspect of the present invention there is provided a skin pricking Lancet. The skin pricking lancet comprises a housing defining an opening in a proximal region thereof, and a lancet mechanism supported substantially within the housing. The lancet mechanism comprises; a needle; a drive spring for driving the needle proximally through said opening along a drive axis from a retracted position to an extended position; a trigger configured in use to be pressed against a user's skin to move the trigger along said drive axis from an extended position to a retracted position in order to release the drive spring; and one or more features cooperating with said trigger to lock the trigger in said retracted position following movement of the trigger to that retracted position.

As an option the skin pricking lancet comprises a frame located within said housing, said feature or features being provided by the frame. The frame may have a substantially "U" shaped cross section, with the bite of the frame being located at a distal end of the housing.

As an option, the feature or features are provided on an inner surface of the housing.

As an option, the trigger is engaged with the drive spring such that movement of the trigger from the extended position to the retracted position cocks the drive spring prior to releasing it. The trigger may extend through the opening in the housing and may define a further opening through which a tip of the needle can pass through upon firing.

As an option the skin pricking lancet further comprises a return spring, acting between the trigger and a needle carrier within which the needle is mounted, and arranged to withdraw the tip of the needle through the opening in the trigger after firing.

As an option the trigger comprises one or more outwardly biased legs arranged to engage with a needle carrier within which the needle is mounted, when the trigger is in the extended position and prior to the trigger reaching the retracted position, said feature(s) being configured to allow the biased leg(s) to expand radially upon the trigger reaching said retracted position, thereby locking the trigger in the retracted position whilst releasing the needle carrier and thereby releasing the drive spring.

According to a fourth aspect of the present invention there is provided a skin pricking lancet comprising an enclosure containing a lancet mechanism, the enclosure defining a housing and cap joined together by one or more features such that permanent removal of the cap from the housing can be achieved by breaking the or each feature, wherein the feature or features provide the only means of coupling between the cap and the housing such that the lancet cannot be re-capped following removal of the cap.

Preferably, the feature or features that join the cap and the housing together are seamless continuations of the cap and housing material.

DETAILED DESCRIPTION

There will now be described a skin pricking lancet comprising a thermoformed enclosure that provides both a housing for a lancet mechanism and a cap for protecting the lancet and maintaining sterility prior to use. Such an enclosure may allow for lower production costs and/or higher production quality.

A thermoforming process typically involves heating a rigid or semi-rigid plastic sheet such that it becomes pliable, followed by pressing the pliable plastic into a desired shape. This latter step can be done in a variety of ways, such as for example vacuum forming, pressure forming, or using a matched die. Once cooled, the resulting moulded impression may then be cropped to the correct size, and skeletal waste reintroduced back into the process after reprocessing.

Figure 1:
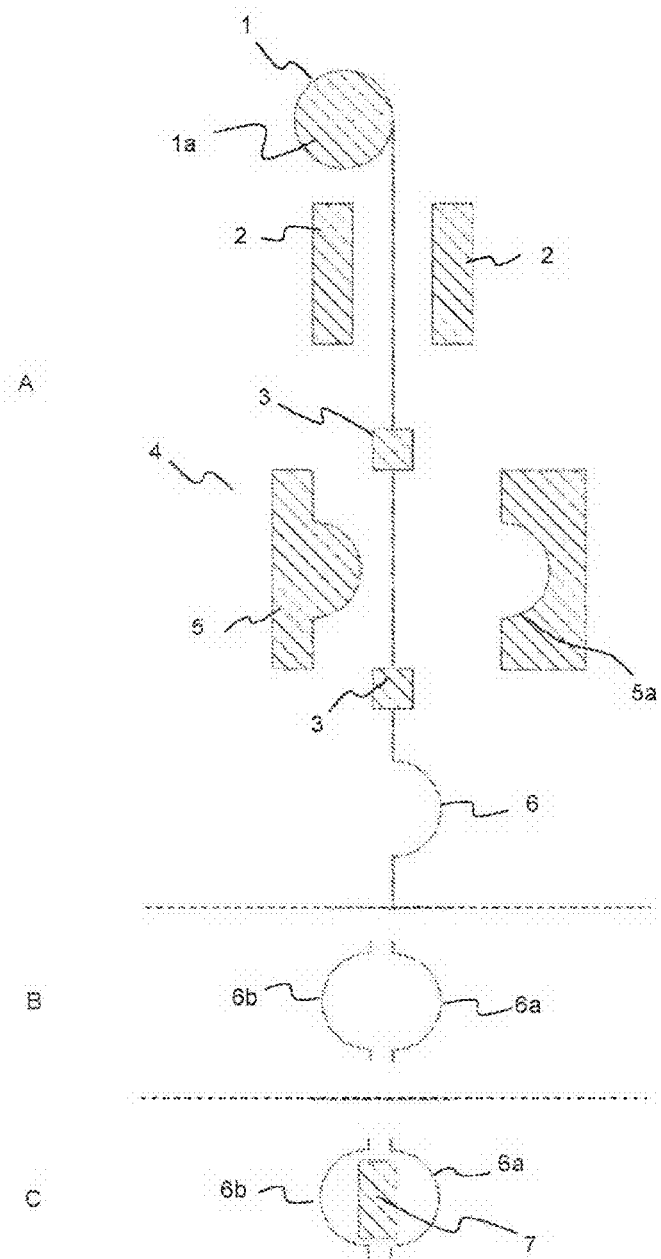
FIG. 1 illustrates schematically a production line for producing lancets.

FIG. 1 illustrates schematically a production line for producing skin pricking lancets and employing a thermoforming process. The horizontal dashed lines in FIG. 1 separate different stages of the production line process, A, B and C. In process stage A, a suitable thermoforming plastic film 1 is provided on a roller 1a. The film 1 may for example have a thickness of between 0.1 and 10 mm, but preferably between 0.4 and 1.5 mm. The film 1 is guided in a step-wise manner to a mould forming area 4 by intermediate rollers (not shown). Before entering the mould forming area 4, a portion of the film 1 is heated by one or more heaters 2 in order to make it pliable. Once the portion of the film is pliable, the mould forming area 4 opens up to allow the portion of the pliable film to be fed into the mould forming area 4. Once the portion has entered the mould forming area 4, the portion is clamped in place by clamps 3, and the intermediate rollers temporarily halt advancement of the film 1. The mould forming area 4 comprises matching male 5 and female 5a mould halves which close around the portion and force it into the shape defined by the mould. Having taken the shape of the mould, the portion cools, regaining rigidity. The mould forming area 4 then opens up to allow a moulded enclosure section 6 to be removed from the mould forming area, and a new section of the film 1 to enter. This process can be carried out quickly and efficiently, resulting in many enclosure sections 6 being created in a short amount of time. It will be appreciated that, whilst the moulded shape in FIG. 1 is semi-circular in cross-section, in practice the shape is more complex.

Process stage B shows two lines of formed plastic films being brought together. The film forms are substantially identical but one is inverted relative to the other. These films could, for example, be produced using two parallel production lines according to stage A. The enclosure sections 6a are arranged to be married up with respective enclosure sections 6b. Process stage C shows a lancet mechanism 7 being located between the two sections 6a,6b which are then hermetically sealed to form an enclosure 8 containing the lancet mechanism 7. The two sections 6a,6b may be sealed together using a heat-sealing method. Examples of heat sealing methods include using hot bar sealers, continuous heat sealers impulse heat sealers, hot melt adhesives, hot wire sealing, fusion bonding, hot-gas welding, induction sealing, vibration welding, and ultrasonic welding. Alternative methods may be used to connect the two sections 6a,6b together, such as by using an adhesive.

After the sections 6a,6b have been sealed together, enclosures are separated from the advancing films, e.g. using a guillotine. Some further trimming to remove excess material may also be performed if required. Of course, this process (FIG. 1) is only exemplary and other processes may be contemplated. For example, the enclosure sections 6a,6b may be separated from the respective films after moulding but prior to joining them together around the lancet mechanism 7. Alternative forming methods may also be used, such as pressure forming, where pressure is applied on the non-mould side of the sheet, pushing it against a mould, or vacuum forming, where a vacuum is created on the mould side of the sheet and atmospheric pressure pushes the sheet against the mould.

Plastics that may be used in the thermoforming process for the enclosure sections 6a,6b include, but are not limited to: ABS; Acrylic; Kydex; Noryl; PETG; Polycarbonate; Polystyrene (HIPS); Polysulfone; PVC; Radel R; Ultem; TPO; PET; Polypropylene; PPS; PTFE; UHMW-PE; HDPE; LDPE; Nylon; Acetal; PBT; and PEEK.

Figure 2:
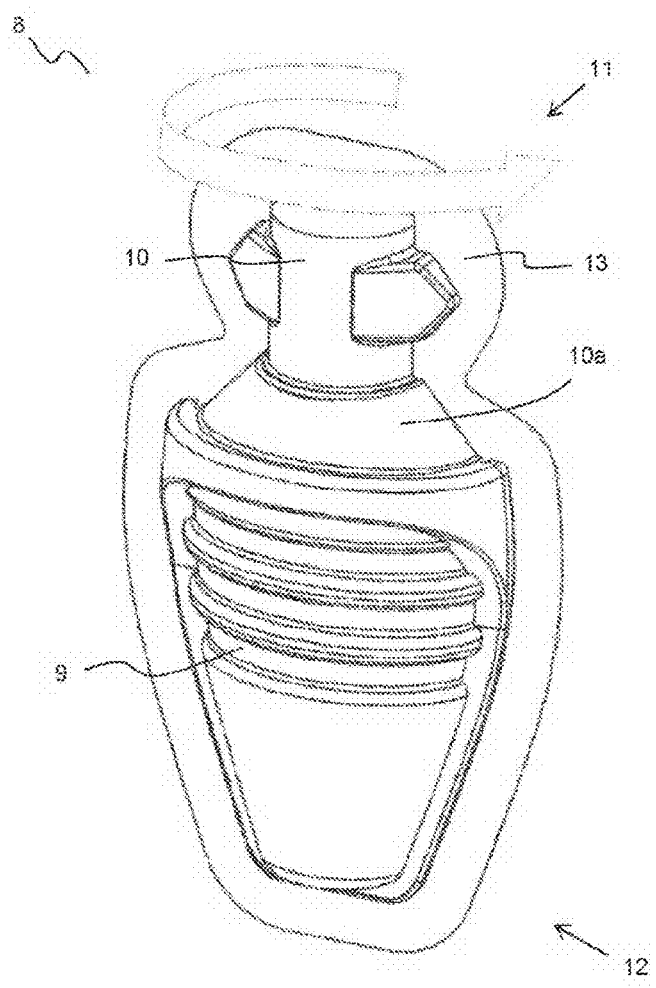
FIG. 2 illustrates an external view of a lancet.

FIG. 2 shows an assembled enclosure 8 containing the lancet mechanism 7. The enclosure has a proximal end 11 and a distal end 12. The enclosure 8 defines a housing 9 which substantially houses the lancet mechanism 7, and a cap 10. It will be readily appreciated that the housing 9 and the cap 10 at this stage form an integrated enclosure unit. Due to the structural properties of the neck region, at the junction between the cap 10 and the housing 9, twisting of the cap 10 relative to the housing 9 allows the user to break the junction and hence remove the cap 10 from the housing 9. A score (not shown) substantially around a junction between the cap and the housing may be created to facilitate breaking of the cap from the housing. The score may be added after the enclosure has been created, or during the moulding process. When the cap 10 is removed, the proximal end of the lancet mechanism 7 is exposed.

The shape of the cap 10 is designed to assist removal of the cap from the housing. In particular, flanges 13 project outwardly from the cap in order to amplify the torque that is applied by the user, and to assist with gripping of the cap. Additionally, or alternatively, the cap may be provided with ridges (not shown) to aid gripping by the user.

Figure 3:
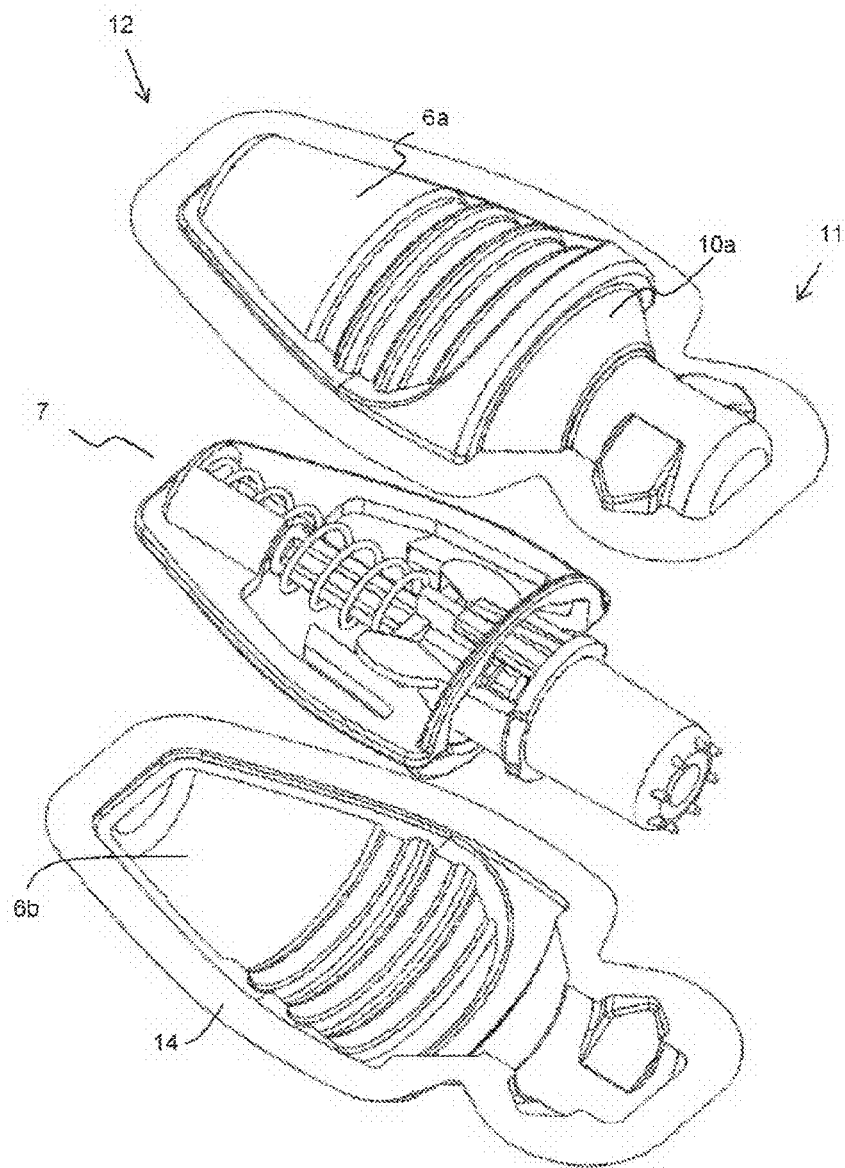
FIG. 3 illustrates an exploded view of the lancet of FIG. 2.

FIG. 3 shows the skin pricking lancet with the two halves of the enclosure 6a,6b opened to expose the lancet mechanism 7. As can be seen in this view, the enclosure sections 6a,6b have flanges 14 running along their edges in order to provide a greater contact surface area for heat sealing the enclosure sections together. In the assembled device these flanges may also assist the user to grip the enclosure housing 9.

The housing 9 part of the enclosure 8 is arranged to structurally support the lancet mechanism 7 during use. In particular, the enclosure 8 is shaped so as to provide a tight fit, e.g. an interference fit, for the lancet mechanism 7 within the enclosure 8, ensuring that the mechanism 7 is held firmly in place even after removal of the cap 10. The neck region 10a of the housing also narrows in the proximal direction to prevent the lancet mechanism falling out of the housing following removal of the cap. Optionally or additionally, an adhesive may be used to secure the lancet mechanism 7 in place.

As well as allowing for low cost production of lancets, the process described here results in a device which, after separation of the cap 10 from the housing 9, provides a clear visual indication of use. In particular, as it is not possible to reattach the cap 10 to the housing 9 (at least in a simple manner which does not expose the break), a user will be left in no doubt that a used device has indeed been used, significantly reducing the risk of confusion and attempted re-use.

The above described embodiment provides several further benefits. The thermoforming process in particular is a more efficient and therefore cost-effective process for producing skin pricking lancets than, for example, processes relying on injection moulding. Furthermore, thermoforming allows for a very thin enclosure section to be produced, which results in a lower total mass, and lower associated radiation sterilization costs if such a sterilization process is employed. A thermoforming-based process may also result in lower waste, since any excess material that is cropped from the moulded parts may be reused in the process.

Thermoforming also facilitates the addition of surface decoration as the plastic film 1 may be pre-printed.

Figure 4:
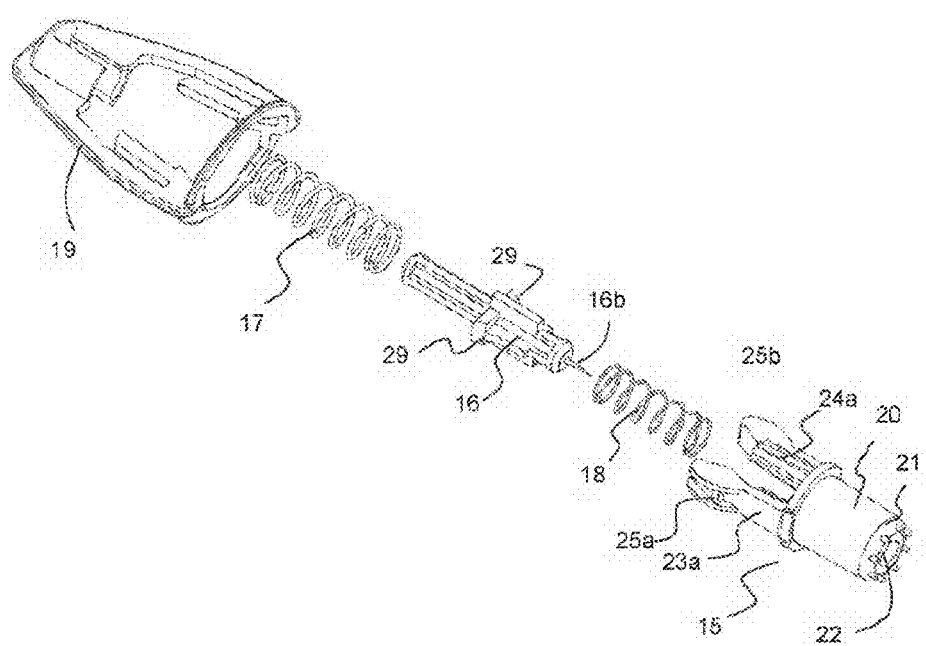
FIG. 4 illustrates an exploded view of a lancet mechanism of the lancet of FIG. 1.
Figure 5:
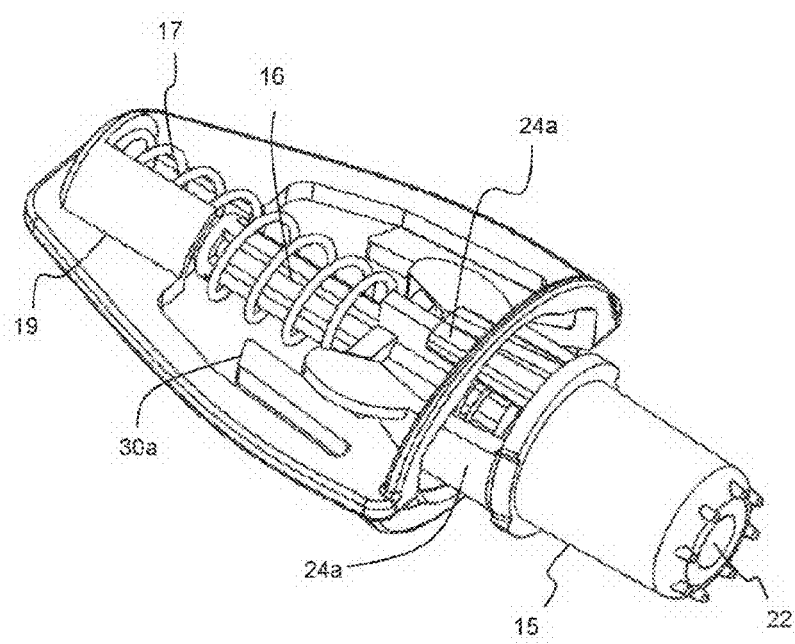
FIG. 5 illustrates a perspective view of the lancet mechanism.
Figure 6:
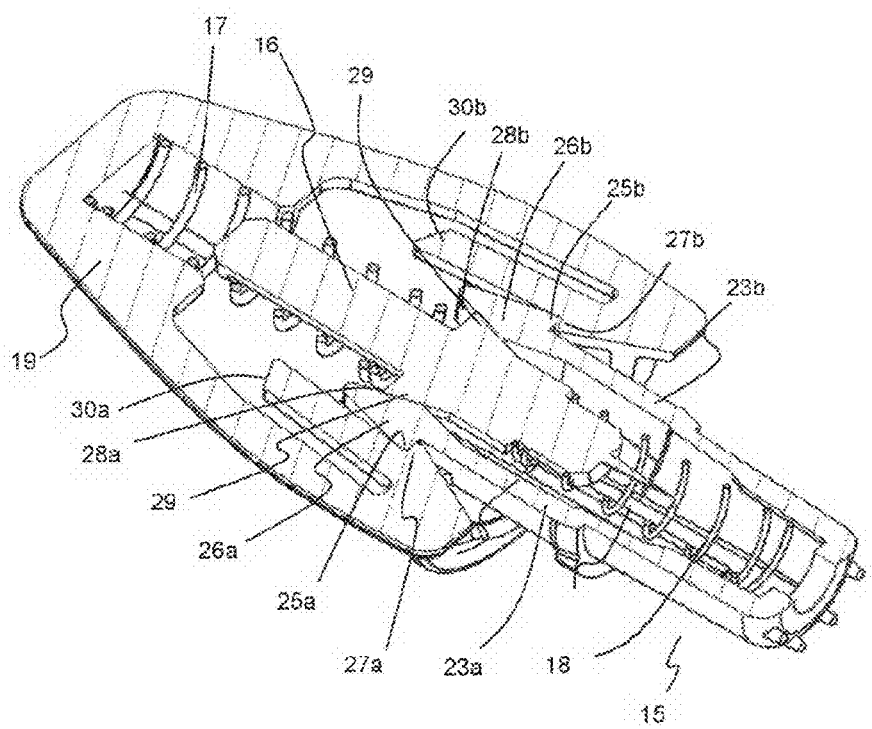
FIG. 6 illustrates a first cross sectional view of the lancet mechanism of FIG. 5.
Figure 7:
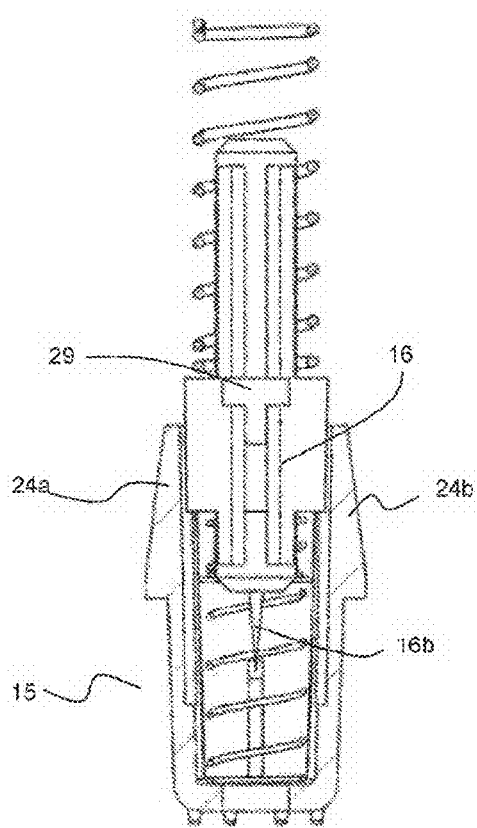
FIG. 7 illustrates a second cross sectional view of the lancet mechanism.

FIG. 4 shows an exploded view of the lancet mechanism 7, which comprises a trigger 15, needle carrier 16 having a needle 16b, drive spring 17, return spring 18, and a support frame 19. FIG. 5 shows a perspective view of the lancet mechanism in an unfired position, and FIG. 6 shows a horizontal cross section through the lancet mechanism in an unfired position. FIG. 7 shows a cross sectional view through the lancet mechanism 7, in the plane perpendicular to the frame 19 (note that the frame 19 is not shown in FIG. 7). As shown in these figures, the drive spring 17 sits within the support frame 19 and the distal end of the needle carrier 16 sits coaxially within the drive spring 17. The return spring 18 sits within the trigger 15 and extends coaxially over a proximal end of the needle carrier 16. The support frame has a substantially "U" shaped cross-section, with the bite of the frame being located at the distal end of the housing.

The trigger 15 comprises a nose 20 having a front face 21 which acts as a surface for pressing against the user's skin, and has an aperture 22 through which the needle 16b may protrude. The front face 21 has a textured surface so as to reduce discomfort by providing a tactile sensation when placing the front face 21 against the user's skin. The trigger has four legs which extend in a distal direction from the nose 20, two of the opposed legs 23a, 23b being flexible in a radial direction and two of the opposed legs 24a, 24b being substantially inflexible. During assembly of the lancet mechanism 7, the trigger is pushed into the frame 19, and the legs 23a, 23b are pressed inwardly by a tapered portion of the frame 19. The outer surface of the flexible legs 23a, 23b are provided with shoulders 25a, 25b formed on feet 26a, 26b which abut corresponding shoulders 27a, 27b on the frame 19 so as to snap the trigger 15 within the frame 19, and prevent the trigger 15 from being removed. The feet 26a, 26b have an inner surface 28a, 28b which engages with a proximal surface of a lip 29 on the needle carrier 16.

Figure 10:
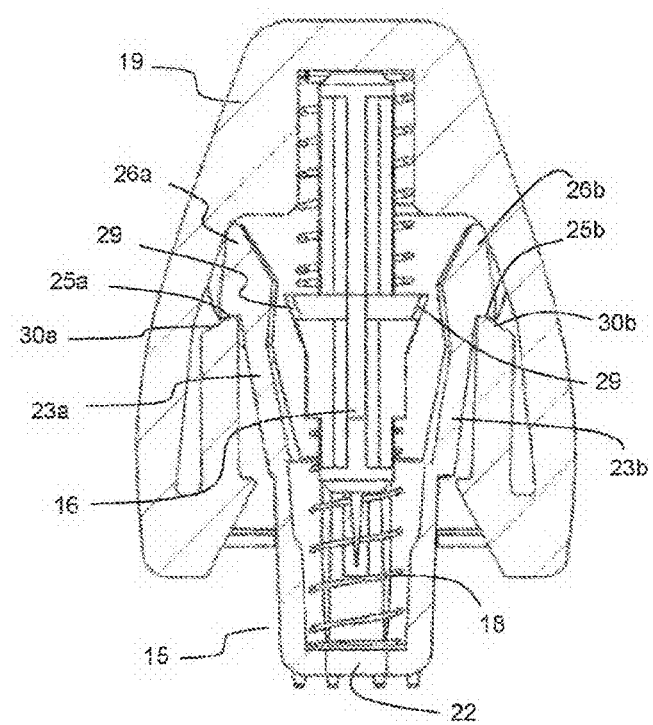
FIG. 10 illustrates a cross sectional view of the lancet mechanism with the trigger in a retracted position.

The trigger 15 is movable relative to the frame 19 along a firing direction of the mechanism from an extended position (unfired position) to a retracted position (lancet release position). The frame 19 has a pair of locking shoulders 30a, 30b, arranged such that when the trigger has travelled a pre-determined distance, the shoulders 25a, 25b formed on feet 26a, 26b engage with the locking shoulders 30a, 30b, which prevents proximal movement of the trigger 15 (shown in FIG. 10).

The substantially inflexible legs 24a, 24b on the trigger 15 may interact with the frame 19 or housing 9 to help maintain alignment of the trigger relative to the frame or housing 9. For example, the legs 24a, 24b may cooperate with grooves (not shown) on the frame 19 or the housing 9 an as to help prevent rotational movement of the trigger 15 relative to the frame 19 or housing 9.

FIGS. 8 to 12 show how the components of the lancet mechanism 7 interact as the skin pricking lancet is used by a user. Reference should be made for example to FIGS. 2 and 3 to understand how the mechanism fits within the enclosure 8 prior to and following removal of the cap. Of course it will be appreciated that the mechanism may be used with other enclosures such as traditional injection moulded enclosures.

Figure 8:
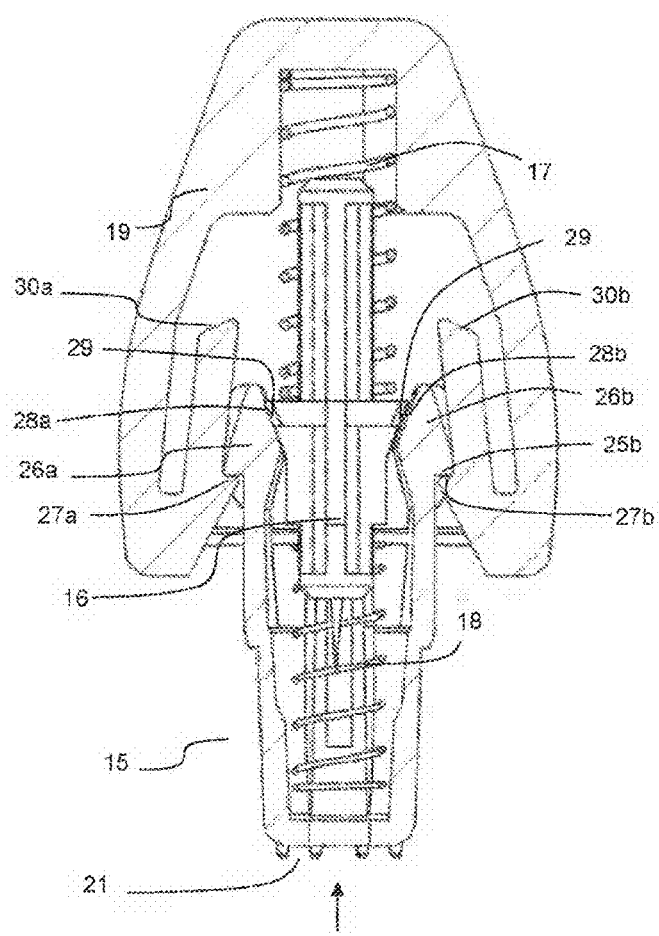
FIG. 8 illustrates a cross sectional view of the lancet mechanism with a trigger in a first extended position.
Figure 9:
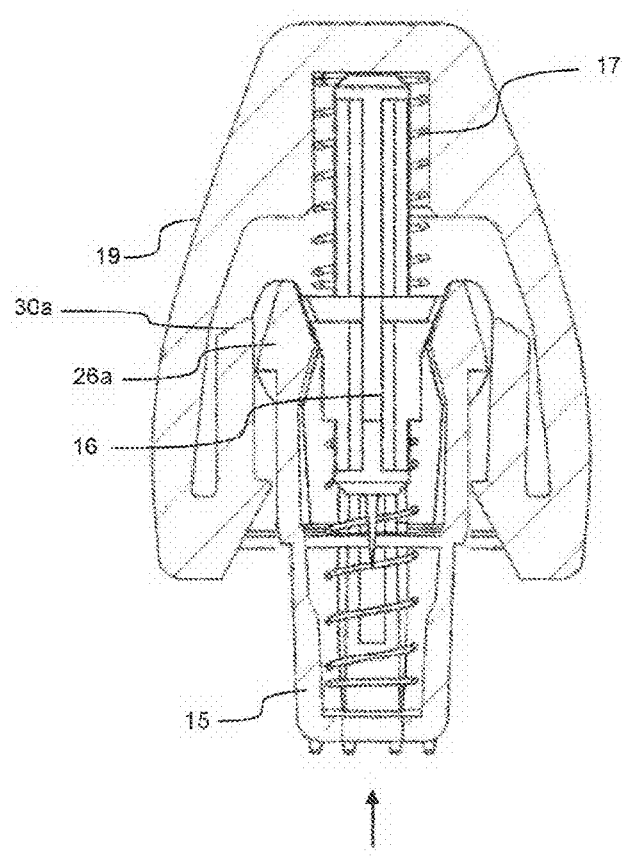
FIG. 9 illustrates a cross sectional view of the lancet mechanism with the trigger in an intermediate position.

Once the user has removed the cap 10 (FIG. 2), the trigger's front face 21 is exposed. Initially the trigger 15 is in the unfired position, i.e. the extended position. The user places the front face 21 against the skin and pushes the skin pricking device towards the skin. The arrow in FIG. 8 shows the direction of the reaction force in response to the user pushing the skin pricking lancet towards the skin. The trigger 15 is effectively pushed into the enclosure 8.

Figure 11:
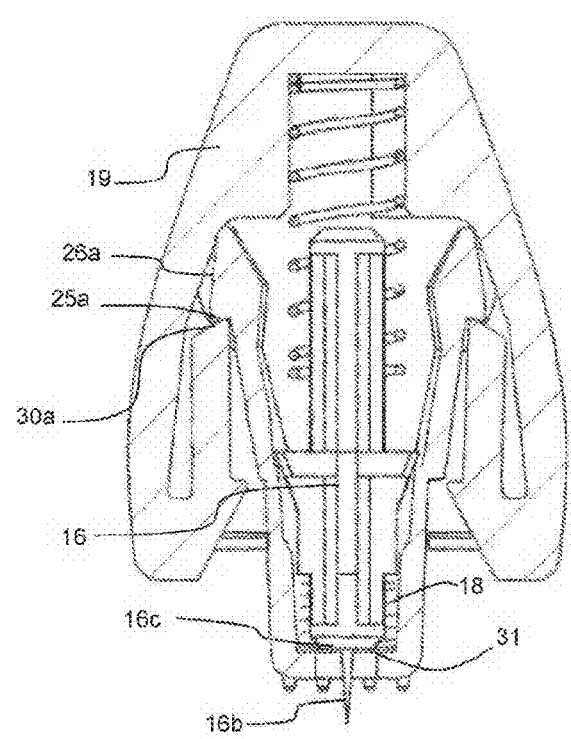
FIG. 11 illustrates a cross sectional view of the lancet mechanism with a needle tip exposed.
Figure 12:
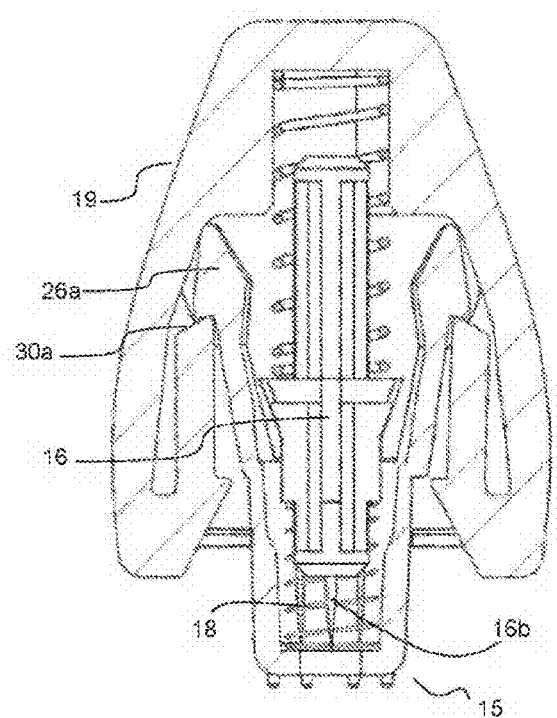
FIG. 12 illustrates a cross sectional view of the lancet mechanism with the needle tip retracted.

As the trigger 15 travels into the housing 9, the needle carrier 16 is also displaced due to the interaction between the inner surfaces 28a, 28b of the feet 26a, 26b and the lip 29 of the needle carrier 16. This causes the drive spring 17 to compress (shown in FIG. 9). When the trigger 15 reaches the retracted (lancet release) position, the legs 23a, 23b splay outwards (shown in FIG. 10), disengaging the feet 26a, 26b from the lip 29. The outer shoulders 25a, 25b of the splayed feet abut the locking shoulders 30a, 30b, holding the trigger in the retracted position. With the feet 26a, 26b disengaging from the lip 29, the needle carrier 16 is then free to travel in the proximal direction under the force provided by the now expanding drive spring 17. The needle 16b enters the aperture 22 in the front face 21 of the trigger 15 and travels a required penetration depth beyond the front face 21, piercing the user's skin (FIG. 11).

As the needle carrier 16 travels in the proximal direction, the needle carrier 16 compresses the return spring 18. Once the required penetration depth has been reached, further proximal movement of the needle carrier 16 is prevented due to a front face 16c of the needle carrier coming into contact with a rear side of the front face 31. The compressed return spring 18 is now able to overcome the force generated by the drive spring 17, and pushes the needle carrier 16 in the distal direction, back towards the frame 19. This action removes the needle 16b from the user's finger, and brings the needle 16b within the confines of the trigger 15 (FIG. 12), where it comes to rest. With the needle 16b brought within the confines of the trigger 15, it is no longer exposed and the risk of accidental injury is minimised. Furthermore, due to the fact that the trigger 15 is held in the retracted position, this provides a visual cue to a user that the skin pricking lancet has been used.

It will be appreciated by the person of skill in the art that further modifications may be made to the above described embodiments without departing from the scope of the present invention. For example, while the trigger is described as having two outwardly biased legs, the trigger may have any number of legs. While the description describes fusing two separate enclosure sections 6a, 6b to create the enclosure 8, the enclosure sections may not be separate, but integrally formed on the one piece of material and folded together to define an enclosure.

Aspects described above may be implemented separately. For example, while described in the context of a thermoformed enclosure, the lancet mechanism 8 may be used in any other type of body.

While a frame 19 has been described as providing the functions of holding a trigger in the extended position and the retracted position, it will be appreciated that these functions may be performed by an appropriately shaped enclosure 8, removing the need for a separate frame 19.

The invention claimed is:

1. A method of manufacturing a skin pricking lancet, comprising:
    thermoforming a plastic component by heating a plastic film until pliable, and then shaping the pliable plastic film by bringing opposing first and second parts of a mould together upon opposing first and second sides of the plastic film and thereby forcing the plastic film into a shape of the plastic component by way of said mould, the first and second parts of the mould separating after the plastic film has cooled and retains the shape of the plastic component;
    locating the thermoformed plastic component around a lancet mechanism, where said lancet mechanism includes a needle, a drive spring, and a trigger; and
    assembling the located plastic component to form a hermetically sealed enclosure surrounding the lancet mechanism,
    the plastic component being formed and assembled to form a housing and a cap attached to the housing, the housing configured to structurally support the lancet mechanism during use, and the cap being breakable from the housing to facilitate firing of the lancet mechanism.

2. The method of manufacturing a skin pricking lancet according to claim 1, further comprising:
    thermoforming one or more further plastic components,
    wherein said locating includes locating also said one or more further plastic components around the lancet mechanism.

3. The method of manufacturing a skin pricking lancet according to claim 1, wherein
    one or more further plastic components are located around the lancet mechanism, and
    the located plastic component and the one or more further plastic components are joined together by heat sealing abutting peripheral edges thereof.

4. The method of manufacturing a skin pricking lancet according to claim 1, wherein the thermoformed plastic component has a thickness of between 0.4 and 1.5 mm.

5. The method of manufacturing a skin pricking lancet according to claim 1, further comprising:
    creating a score around the sealed enclosure at a junction between the housing and the cap in order to facilitate breaking of the cap from the housing.

6. The method of manufacturing a skin pricking lancet according to claim 1, further comprising:
    irradiating the sealed enclosure in order to sterilize the interior of the sealed enclosure including the lancet mechanism.

7. The method of manufacturing a skin pricking lancet according to claim 1, wherein the thermoformed plastic component forms both a part of the cap and a part of the housing.

8. The method of manufacturing a skin pricking lancet according to claim 1, further comprising:
    forming a narrowing of the sealed enclosure at a junction between the housing and the cap.

* * * * *